United States Patent [19]

Daly et al.

[11] Patent Number: 5,062,120
[45] Date of Patent: Oct. 29, 1991

[54] UNDERWATER FRAZIL ICE DETECTOR

[76] Inventors: Steven F. Daly, P.O. Box 148, Piermont, N.H. 03779; John H. Rand, P.O. Box 203, Cornish Flat, N.H. 03746

[21] Appl. No.: 343,237

[22] Filed: Apr. 26, 1989

[51] Int. Cl.[5] .................... G01N 25/04; G08B 19/02
[52] U.S. Cl. .............................. 374/143; 73/170 R; 340/580; 374/16; 417/38
[58] Field of Search ............... 374/135, 210, 142, 136, 374/143; 62/139; 340/580, 581; 210/774, 747, 170, 111; 55/215

[56] References Cited

U.S. PATENT DOCUMENTS

| | | |
|---|---|---|
| 2,541,512 | 2/1951 | Hahn . |
| 2,739,302 | 3/1956 | Timbie . |
| 3,077,988 | 2/1963 | Anderson et al. . |
| 3,164,820 | 1/1965 | Hulett .................... 340/581 |
| 3,613,063 | 10/1971 | Ciemochowski ............. 340/581 |
| 3,686,926 | 8/1972 | Miller et al. . |
| 4,210,021 | 7/1980 | Vykhodtsev et al. . |
| 4,222,044 | 9/1980 | Boschung .................... 340/580 X |
| 4,263,805 | 4/1981 | Isley et al. . |
| 4,497,181 | 2/1985 | Kocher et al. ................ 62/139 |
| 4,755,062 | 7/1988 | Meyer ......................... 374/16 |

Primary Examiner—Daniel M. Yasich

[57] ABSTRACT

An underwater frazil ice detector is disclosed comprising channel means disposed underwater for moving water therethrough, means for drawing water through said channel means, screen means disposed in and across said channel means so that water drawn therethrough by said water drawing means passes through said screen means, pressure detecting means disposed in said channel means and downstream of said screen means for detecting pressure differential across said screen means, whereby flow of water through said screen means is constricted when frazil ice forms thereon, creating an increased pressure differential across said screen means and thereby indicating the presence of frazil ice.

41 Claims, 4 Drawing Sheets

UNDERWATER FRAZIL ICE DETECTOR

STATEMENT OF GOVERNMENT INTEREST

The invention described and claimed herein may be manufactured and used by or for the Government of the United States of America for governmental purposes without the payment of royalties thereon or therefor.

FIELD OF THE INVENTION

The invention relates to an apparatus and method of detecting underwater frazil ice.

BACKGROUND OF THE INVENTION

Frazil ice is formed in turbulent, supercooled water. It is normally well distributed throughout the depth of the flow, ranging in size from 50 microns to several centimeters. Frazil ice can adhere to underwater objects. In the winter season, it commonly causes blockage of water intakes by adhering to the water intake trash rack. Prior to this invention, there is no device for the detection of underwater frazil ice. Previous methods used for detection included inference by measuring the rate of change of water temperature near the freezing point, monitoring pressure head loss or discharge reduction due to freeze up of an inlet, or monitoring meteorological conditions. None of the aforementioned methods provides an unambiguous means of detecting frazil ice.

Related prior art discloses ice detectors for use on an aircraft, as illustrated by Hahn, U.S. Pat. No. 2,541,512; Timbie, U.S Pat. No. 2,739,302; and Vykhodtsev, U.S. Pat. No. 4,210,021. Other related art discloses devices which sense the clogging of filters due to pressure change. Illustrative references are Isely, U.S. Pat. No. 4,263,805; Miller, U.S. Pat. No. 3,686,926; and Anderson, U.S. Pat. No. 3,077,988.

OBJECTS OF THE INVENTION

It is an object of the invention to provide a device that will directly detect underwater frazil ice.

It is another object of the invention to provide an underwater frazil ice detector that protects itself from becoming ice covered and thus becoming non-effective.

It is yet another object of the invention to provide an underwater frazil ice detector that will transmit a clear and unambiguious signal when frazil ice is detected.

It is still another object of the invention to provide a compact underwater frazil ice detector.

It is another object of the invention to provide an underwater frazil ice detector that is easy to maintain.

It is a further object of the invention to provide an underwater frazil ice detector that mimics the formation of frazil ice in a water intake trash rack.

It is an additional object of the invention to provide direct detection of the presence of frazil ice by measuring pressure in a fluid flow.

It is still an object of the invention to provide direct detection of the presence of frazil ice by measuring the flow rate in a fluid flow.

It is an object of the invention to provide direct detection of the presence of frazil ice by measuring the current draw of a drive means for causing fluid flow.

It is a further object of the invention to provide a device for detecting frazil ice which is self-heating so that the instrument itself will not ice up.

It is an object of the invention to provide an underwater frazil ice detector which is self cleaning.

It is still another object of the invention to provide an underwater frazil ice detector that will alert operators of potential freeze-up of a water intake in sufficient time so that proper action can be taken to prevent total blockage of the intake by frazil ice.

It is another object of the invention to provide an underwater frazil ice detector that permits automatic activation of alarms and de-icing equipment.

It is yet another object of the invention to provide an underwater frazil ice detector that is independent in operation and does not require manual supervision.

It is a further object of the invention to provide a method for detecting and avoiding underwater frazil ice.

In summary, the invention will provide an apparatus, system and method for directly detecting and avoiding underwater frazil ice.

DESCRIPTION OF THE INVENTION

FIGURE 1

An underwater frazil ice detector system A comprises a detector B, a control unit C, temperature sensors D and G, a remote annunciator E and a de-icing control unit F.

Figures 1, 5:
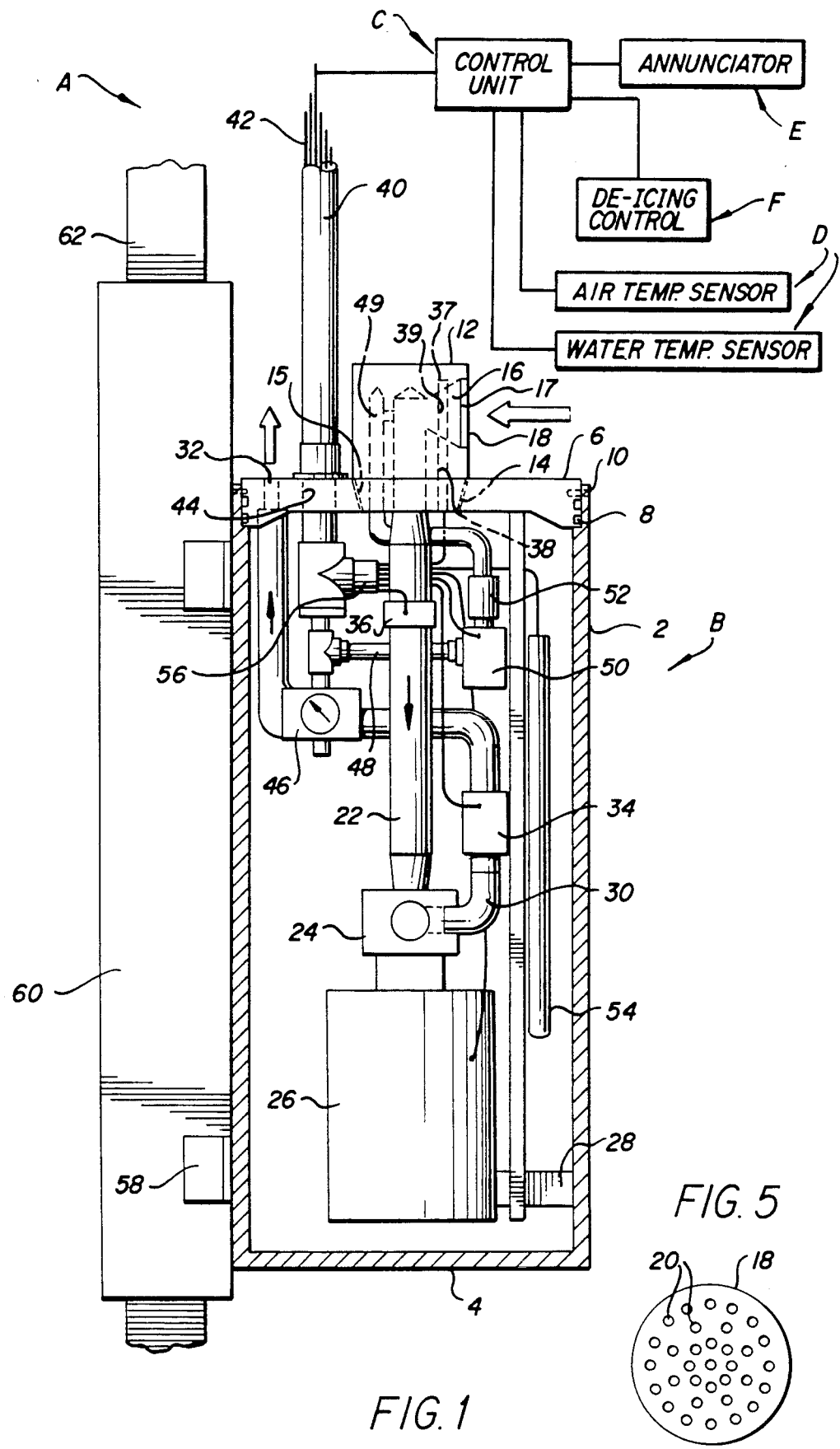
FIG. 1 is a fragmentary side elevational view of the underwater frazil ice detector a portion of which is shown in phantom lines. The detector is shown mounted on a support bracket and diagramatically connected to a control unit.
FIG. 5 is a front elevation of the screen used in the invention.

The detector B, disposed underwater, includes a housing 2 made from a stainless steel pipe or other material, typically 10 inches in diameter, 24 inches long and schedule 20. One end of the housing 2 is enclosed by an end flange 4 welded thereto while the other end is enclosed by an intake housing flange 6. Static "O" rings 8 and a plurality of set screws 10 provide a water tight closure between the intake housing flange 6 and housing 2. The intake housing flange 6 is removable to gain access to various components inside the housing 2. Mounted on the intake housing flange 6 is an intake housing 12 which includes a threaded end 14 for attachment to the intake housing flange 6. Intake housing flange 6 has a threaded hole 15 which cooperates with the threaded end 14 of the intake housing 12. Intake housing 12 is made of a stainless steel or other material, solid body cylinder having a water intake channel 16. An inlet opening 17 is in fluid communication with the water. An intake screen 18, as best shown in FIG. 5, made of a stainless steel disk and having a plurality of holes 20 covers the opening 17. Intake screen 18 is preferably ¼" thick disk, 2¼" diameter with 64 each ⅛" diameter holes drilled therethrough. Intake screen 18 is attached to intake housing 12 by means of a set screw (not shown). Intake housing 12 includes an air discharge port 49 disposed to direct compressed air substantially transversely to screen 18 to backflush the screen 18.

A suction hose 22 is operably connected to the intake channel 16 and to water pump 24. An electric motor 26, mounted in a support shelf 28, drives the pup 24. Pump 24 is preferably rated at ⅛ hp, 450 rpm, 15 gpm and 10 feet head. A discharge hose 30 is connected to the discharge side of pump 24 to a water discharge port 32 located on intake housing flange 6 and in fluid communication with the water. The discharge port 32 is disposed away from the inlet opening 17 so that discharged water is not redrawn through the screen 18. Preferably, suction hose 22 and discharge hose 30 is ⅜" flexible hose. A flow sensor 34 is interposed in the discharge hose 30 and in fluid communication therewith to monitor the water flow in the pumping circuit. When a reduction or absence of flow occurs, the flow sensor 34 provides a signal to the control unit C. A pressure sensor 36 is disposed inside the suction hose 22. Pressure sensor 36 measures the pressure differential across the intake screen 18. An increase in pressure differential to a critical value activates the pressure sensor 36 to provide a signal to the control unit C.

A plurality of intake heaters 38 (only one is shown for clarity of drawing) are circumferentially disposed in the intake housing 12 in respective recesses 39. Preferrably, heaters 38 have a total power rating of 800 watts.

A conduit 40 carries a plurality of control wires 42 and compressed air into the interior of detector B. Conduit 40 connects to the intake housing flange 6 through a hole 44 with a water tight seal. The compressed air is preferrably at 100 psi. Conduit 40 is preferably a ⅜" hydraulic/pneumatic hose. An air regulator 46 is operably connected to the end of the conduit 40 inside the housing 2. The air regulator 46 is preferably set at 5 psi and provides a positive pressure inside the housing 2 to keep the water out. A branch conduit 48 is operably connected to the conduit 40 and terminates at an air discharge port 49 located in the intake housing 12. An air blast solenoid 50 is disposed and in fluid communication with the branch conduit 48. A check valve 52 is interposed between the solenoid 50 and air discharge port 49. The air blast solenoid 50 selectively releases compressed air through the check valve 52 to the air discharge port 49. The blast of compressed air backflushes the screen 18 to dislodge frazil ice or other foreign material. The check valve 52 prevents the water from entering the air line when the air blast solenoid 50 is closed.

A self-regulating heater 54 provides a constant temperature inside the housing 2 for the various components of the detector B.

An electrical connector 56 terminates the control wires 42 in a convenient single location inside the detector B. Individual wires connect to the electrical connector 56 the motor 26, flow sensor 34, air blast solenoid 48, intake heaters 38, pressure sensor 36 and self-regulating heater 54.

Attachment clips 58 mount the detector housing 2 to a slide 60 which cooperates with rail 62. Rail 62 is a square tubular steel rail anchored to an underwater structure 102 at a location where frazil ice is to be monitored. The top of the rails 62 allows removal of the slide 60 and the detector B for inspection and maintenance. The slide 60 is tubular steel with brass rollers (not shown) to facilitate movement of the slide 60 relative to the rail 62. The detector housing 2 is positioned adjacent the underwater structure 102 by moving slide 60 along rail 62.

FIGURE 2

The control unit C controls the operation of the detector B, the de-icing control unit F and the remote annunciator E. Inputs to the control unit C are provided by sensors D and G for air and water temperatures. Control unit C includes an electronic programmable relay controller 64 or a mechanical equivalent with a timer (not shown), a series of display lights A' to H', a series of relays 68, a plurality of connectors 70 and all of the required wiring to interconnect the components. Remote annunciator E having a having a series of status lights A" to F" provides operational status of detector B in a location remote from control unit C. De-icing control unit F includes a relay 72 having a plurality of contacts 74 which control various de-icing equipment such as vibrators, heaters, flow control devices, etc., labeled 1, 2 and 3 in FIG. 3 which may be connected to a water intake trash rack and as well as any and all alarms.

Control unit C also includes a thermostatic switch 76, a thermostat override switch 78 and a test switch 80.

OPERATION

Figure 2:
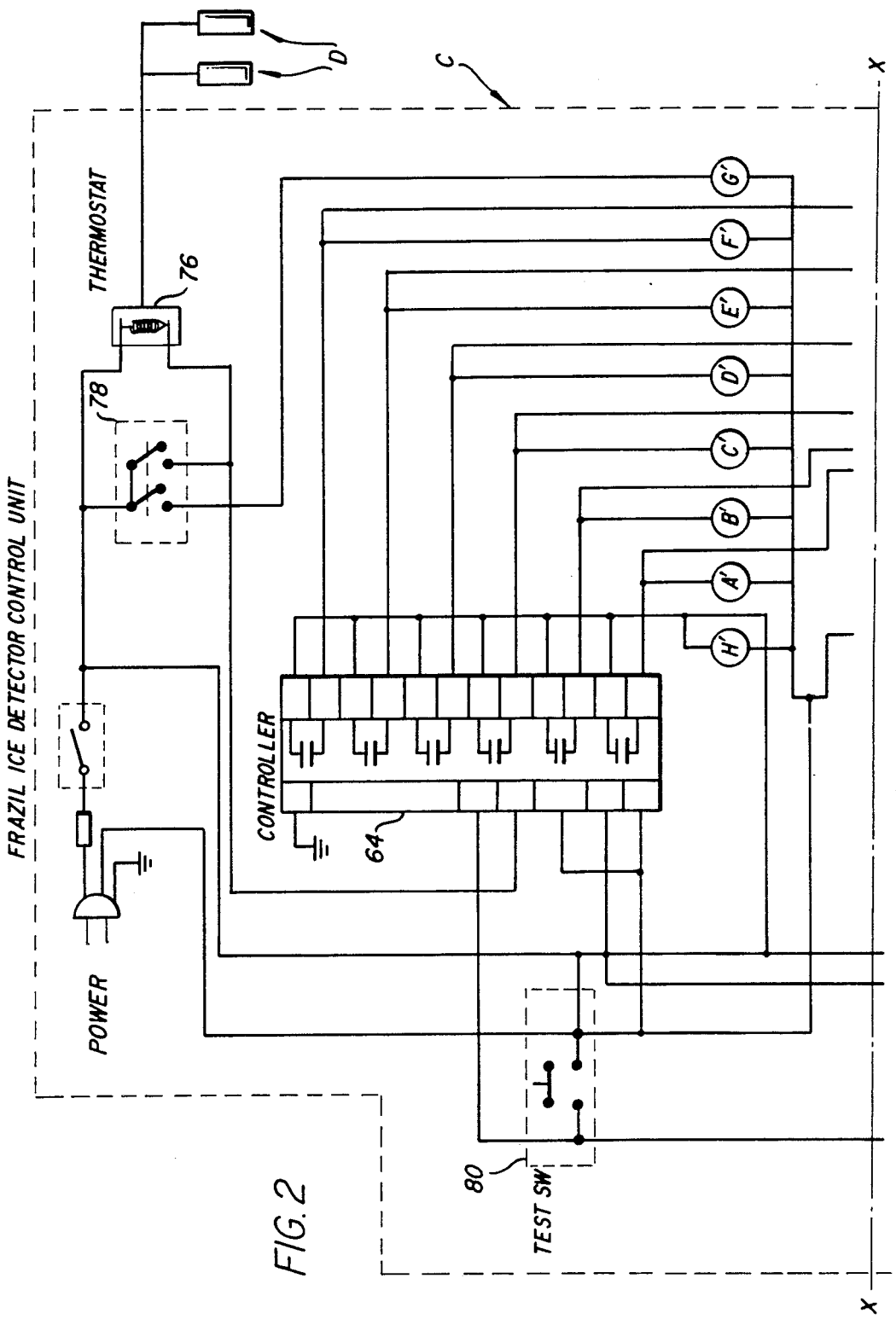
FIG. 2 is a fragment of the electrical schematic diagram of the underwater frazil ice detector system, showing a portion of the control unit. The rest of the schematic diagram extends into FIG. 3 by matching line x—x with line x—x in FIG. 3.
Figure 3:
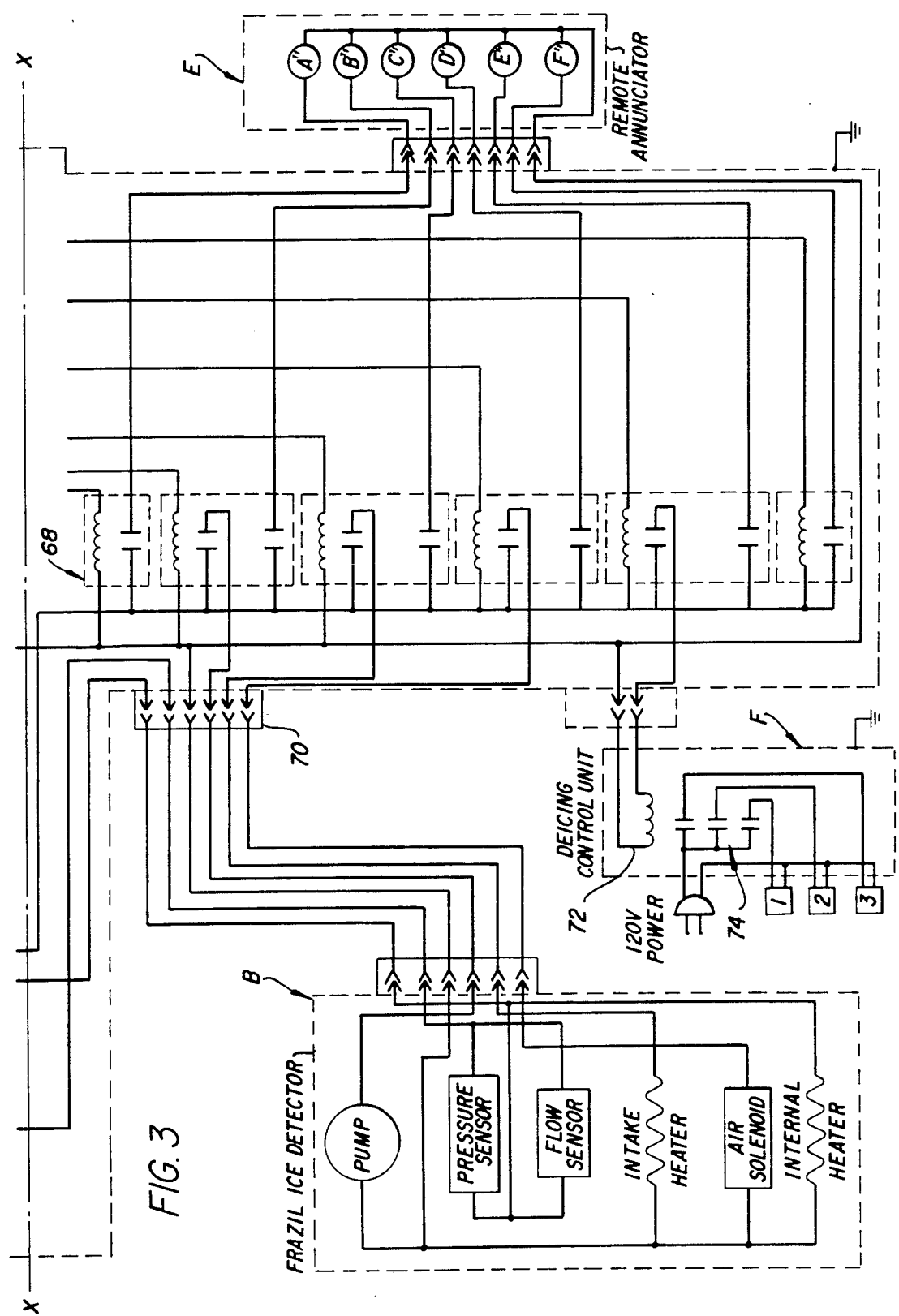
FIG. 3 is a fragment of the electrical schematic diagram of the underwater frazil ice detector system, showing the continuation from FIG. 2 of the schematic diagram of the control unit and the rest of the system. Line x—x matches with line x—x in FIG. 2.
Figure 4:
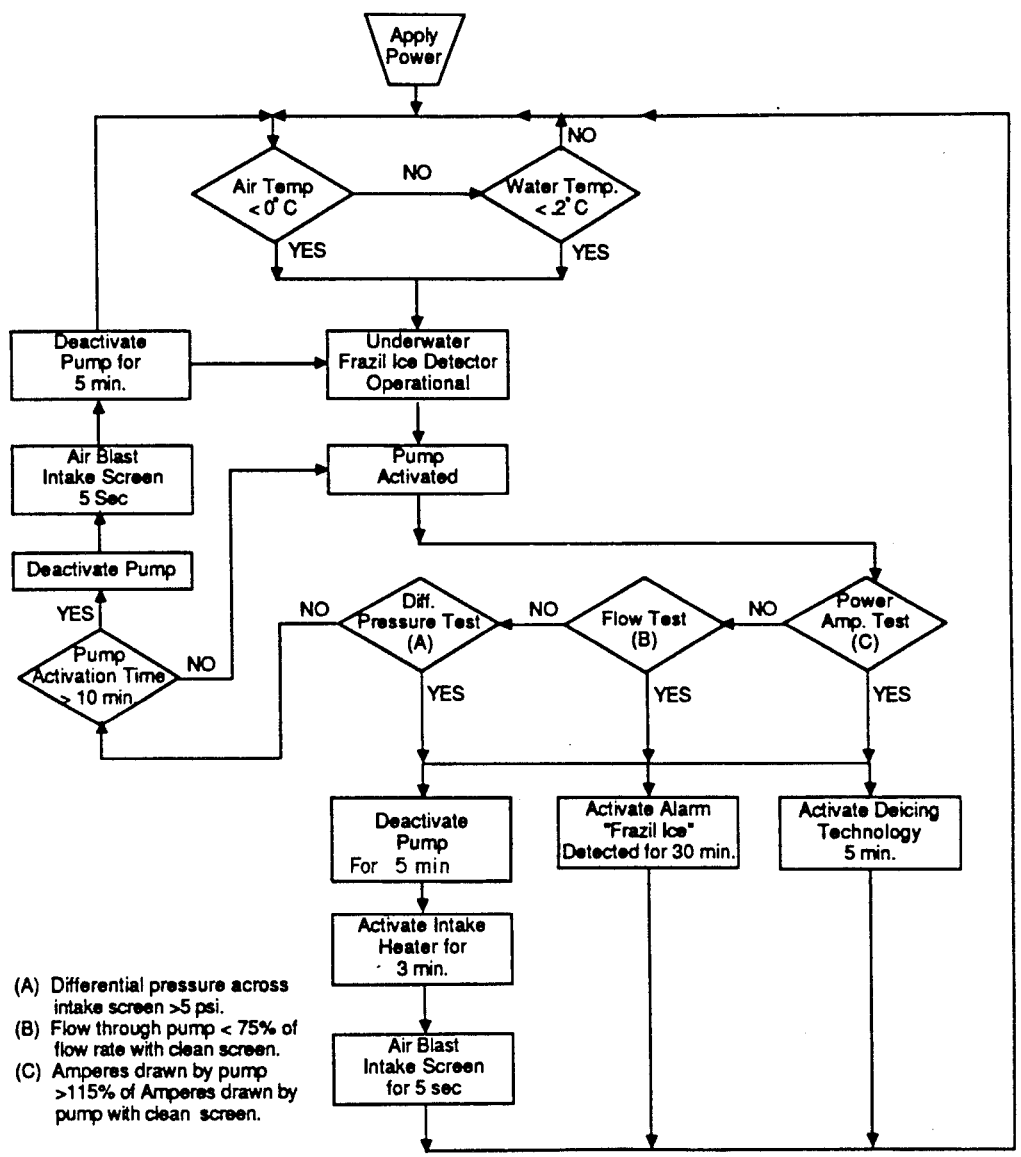
FIG. 4 is a flow chart diagram of a method for detecting and avoiding underwater frazil ice.

FIGURES 2 to 4

Power is applied to the control unit C. Display light H' illuminates to indicate that power is on. If either air or water temperature are of sufficient specific values to activate the thermostatic switch 76, relay 68 activates the motor 26 which drives the pump 24. Display light A' in the control unit C and a status light A" in the remote annunciator illuminate to indicate that the detector B is now operational. Display light B' in the control unit C and a status light B" in the remote annunciator E illuminate to indicate that the pump 24 is running. Relay controller 64 permits the pump 24 to run for a predetermined period of time. Preferably if after 10 minutes, frazil ice is not detected the relay controller 64 deactivates the pump 24 and the associated display and status lights. The air blast solenoid 50 is then activated by the relay controller 64, preferably for 5 seconds, to apply compressed air at 100 psi through the intake screen 18. This clears the screen 18 of any accumulated matter. During this time, display light D' in the control unit C and status light D" in the annunciator E illuminate to indicate the operation of the air blast solenoid 50. The pump 24 remains deactivated preferably for 5 minutes after which time the pump 24 is activated and the cycle is repeated until pump 24 is deactivated again or the intake screen 18 becomes clogged with ice.

If frazil ice is present in the water, the intake screen 18 will become clogged with frazil ice during the activation of the pump 24. Experience with the detector B as herein described has indicated that typical clogging times are between 30 seconds and 3 minutes. Clogging will cause an increase in the differential pressure across the intake screen 18 and a decrease in flow through the pump 24. An increase in the differential pressure across screen 18 activates the differential pressure senor 36 which preferably switches at approximately 5 psi differential pressure. A decrease in flow activates the flow sensor 34 which preferably switches at approximately 75 percent of the original flow rate. Clogging also causes the motor 26 to increase its current draw. Typically, frazil ice is detected when the motor 26 draws 15% more current as detected by motor current detector 100. Detection of an increase in differential pressure, a decrease in the flow rate or an increase in Current draw deactivates the pump 24 and activates the relay 72 in the de-icing control unit F. Display light F' in the control unit C and status light F" in the annunciator E illuminate to indicate that frazil ice has been detected. Relay 72 then operates a combination of de-icing equipment such as vibrators, heaters, flow control devices, etc., connected to a water intake trash rack and as well as any and all type of alarms. Preferably the de-icing equipment is operated for 5 minutes. Display light E' in the control unit C and status light E" in the annunciator E illuminate to indicate that the de-icing equipment is operating. Upon deactivation of the pump 24, intake heaters 38 activate, preferrably for 3 minutes, to melt frazil ice on the screen 18. At the end of 3 minutes, the air blast solenoid 50 activates, preferably for 5 seconds, to backflush the screen 18 of melted frazil ice. Display lights C' and D' in the control unit C and status lights C" and D" in the annunciator E illuminate to indicate the operation of the air blast solenoid 50 and the operation of the intake heaters 38. The pump 24 stays deactivated while the de-icing equipment stays on, preferably for 5 minutes.

The above described cycles will repeat themselves until the thermostat switch 76 opens or until the power to the control unit C is turned off.

Test switch 80 will test the operation of the intake heaters 38, air blast solenoid 50 and the de-icing control unit F. The thermostat override switch 78 can be activated to put the system in operation if the temperature sensors D should malfunction.

The time periods provided above with respect to the operational time of the components of the detector system A could be changed by reprogramming the electronic programmable relay controller 64. The data provided have been found to be appropriate for the specific configuration of the detector B as herein described.

While this invention has been described as having preferred design, it is understood that it is capable of further modification, uses and/or adaptations of the invention following in general the principle of the invention and including such departures from the present disclosure as come within known or customary practice in the art to which the invention pertains, and as may be applied to the essential features set forth, and fall within the scope of the invention or the limits of the appended claims.

We claim:
1. An underwater frazil ice detector, comprising:
   a) channel means disposed underwater for moving water therethrough;
   b) means for drawing water through said channel means;
   c) screen means disposed in and across said channel means so that water drawn therethrough by said water drawing means passes through said screen means;
   d) pressure detecting means disposed in said channel means and down stream of said screen means for detecting pressure differential across said screen means;
   f) whereby flow of water through said screen means is constricted when frazil ice forms thereon, creating an increased pressure differential across said screen means and thereby indicating the presence of frazil ice.
2. A detector as in claim 1, and further comprising:
   a) a water tight housing operably associated with said channel means;
   b) said housing includes an intake opening and a discharge port;
   c) said channel means includes an intake end and a discharge end;
   d) said intake end is operably associated with said intake opening and in fluid communication with the water; and
   e) said discharge end is operably associated with said discharge port and in fluid communication with the water.
3. A detector as in claim 2, and further comprising:
   a) means for pressurizing said housing.
4. A detector as in claim 2, and further comprising:
   a) heater means for keeping the interior of said housing at a constant temperature.
5. A detector as in claim 2, wherein:
   a) said housing includes a removable flange; and
   b) said intake opening and said discharge port of said housing are disposed on said flange.
6. A detector as in claim 5, wherein:
   a) said flange includes seal means for making a water tight connection with said housing.
7. A detector as in claim 6, wherein:
   a) said seal means includes a plurality of resilient "O" rings disposed around the periphery of said flange and cooperates with said housing to provide a water tight connection.
8. A detector as in claim 5, wherein:
   a) said flange includes an intake housing having a water intake channel in fluid communication with said intake opening thereof.
9. A detector as in claim 8, wherein:
   a) said screen is disposed in and across said channel of said intake housing.
10. A detector as in claim 1, and further comprising:
    a) means for clearing said screen means of frazil ice.
11. A detector as in claim 10, wherein:
    a) said clearing means includes a heater.
12. A detector as in claim 11, and further comprising:
    a) air blast means.
13. A detector as in claim 11, wherein:
    a) said intake housing is a solid mass having at least a recess disposed therein; and
    b) said heater is disposed in said recess.
14. A detector as in claim 10, wherein:
    a) said clearing means includes air blast means.
15. A detector as in claim 14, wherein:
    a) said air blast means is operably associated with said channel of said intake housing for blowing compressed air in a backflushing manner across said screen means.
16. A detector as in claim 15, wherein:
    a) said air blast means includes conduit means operably associated and in fluid communication with said channel of said intake housing for conveying compressed air;
    b) solenoid valve means interposed in said conduit means and in fluid communication therewith for selectively releasing compressed air to said screen means; and c) check valve means interposed and in fluid communication between said solenoid valve means and said channel for preventing backflow of water into said conduit means when said solenoid value means is not operating.

17. A detector as in claim 16, wherein:
a) said air blast means includes means for pressurizing said housing; and
b) said pressurizing means includes all air regulator operably connected to said conduit means for selectively releasing compressed air into said housing.

18. A detector as in claim 1, and further comprising:
a) means for mounting said detector underwater.

19. A detector as in claim 18, wherein:
a) said mounting means includes rail means having one portion disposed underwater and another portion disposed above water;
b) slide means which engages and slides along said rail means; and
c) clip means attached to said housing and said slide means.

20. A detector as in claim 1, wherein:
a) said drawing means includes a pump means and a drive means operably associated with said pump means; and
b) said pump means is operably connected and in fluid communication with said channel means.

21. A detector as in claim 20, and further comprising:
a) a support shelf disposed inside said housing for supporting said pump means and said drive means.

22. A detector as in claim 20, wherein:
a) said drive means is a motor; and
b) means for detecting current draw by said motor.

23. A detector as in claim 1, and further comprising:
a) means disposed and in fluid communication with said channel means for detecting flow rate of the water in said channel means.

24. A system for detecting and avoiding underwater frazil ice on an underwater object, comprising:
a) a frazil ice detector disposed underwater;
b) control means operably connected to said detector for controlling the operation thereof;
c) means for sensing air and water temperatures;
d) means for activating said control means in response to detection of specific values of air or water temperatures by said sensing means; and
e) means for providing an alarm upon the detection of underwater frazil ice by said detector.

25. A system as in claim 24, wherein:
a) said activating means includes a thermostat responsive to said temperature sensors.

26. A system as in claim 24, wherein:
a) said detector includes a water tight housing having an intake opening and a discharge port in fluid communication with the water;
b) hose means, disposed inside said housing and including one end of said hose means operably associated and in fluid communication with said intake opening and another end operably associated and in fluid communication with said discharge port, for passing water therethrough;
c) drive means for drawing water through said hose means;
d) screen means disposed in said hose means so that water drawn therethrough by said drive means passes through said screen means;
e) means for clearing said screen means of frazil ice;
f) means for detecting differential pressure across said screen means;
g) means for detecting water flow rate in said hose means;
h) means disposed and in fluid communication with said hose means for detecting water flow rate in said hose means;
i) means for detecting current draw of said drive means; and
j) means for mounting said detector underwater.

27. A system as in claim 26, wherein:
a) said alarming means includes a display light responsive to said detecting means for differential pressure, water flow rate and current draw.

28. A system as in claim 26, and further comprising:
a) a de-icing equipment operably associated with an underwater object; and
b) means operably associated with said control means for activating said de-icing equipment when one of said detecting means reaches critical value.

29. A system as in claim 26, wherein:
a) said control means is operably connected to said drawing means, pressure detecting means, flow rate detecting means, current draw detecting means, de-icing activating means and clearing means.

30. A system as in claim 29, wherein:
a) said control means includes a programmable controller for varying the sequence and period of operation of said drive means and said clearing means.

31. A system as in claim 29, wherein:
a) said control means includes means for indicating operational status of at least one of said drive means, clearing means and detecting means.

32. A system as in claim 29, wherein:
a) said control means includes a remote annunciator to indicate operational status of said detector in a location remote from said control.

33. A system as in claim 32, wherein:
a) said control means includes means for overriding said activating means for said control means.

34. A system as in claim 33, wherein:
a) said control means includes a test switch for testing the operation of said detector.

35. An method for detecting underwater frazil ice, comprising the steps of:
a) positioning an underwater frazil ice detector underwater;
b) monitoring water temperature adjacent the detector and air temperature adjacent the water's surface;
c) activating said detector at specific values of air or water temperature to cause water flow in said detector;
d) subsequently, monitoring the pressure differential between said detector and the water until a specific value i.e. reached indicating the pressure of frazil ice formed on said detector; and
e) activating an indicator for indicating the presence of frazil ice.

36. A method as in claim 35, and further comprising the step of:
a) activating a means for removing frazil ice from said detector.

37. A method as in claim 36, wherein:
a) said step of activating includes applying heat.

38. A method as in claim 36, wherein:
a) said step of activating includes applying air.

39. A method as in claim 36, wherein:
a) said step of activating includes applying heat and air.

40. A method as in claim 35, wherein:
a) said step of activating said detector includes activating and deactivating said detector for a predetermined period of time until frazil ice is detected.

41. A method for detecting underwater frazil ice and avoiding the formation thereof and on an underwater object, comprising the steps of:
a) providing a de-icing equipment operably connected to the underwater object;
b) positioning an underwater frazil ice detector adjacent to said underwater object;
c) monitoring water and air temperatures;
d) activating said detector at specific values of air or water temperature to cause water flow in said detector;
e) subsequently, monitoring pressure differential in said detector until a critical value is reached indicating the presence of frazil ice formed on said detector and said underwater object; and
f) activating said de-icing equipment.

* * * * *